(12) United States Patent
Zhuang et al.

(10) Patent No.: US 8,871,492 B2
(45) Date of Patent: Oct. 28, 2014

(54) **ANTI-DEMENTIA SUBSTANCE FROM *HERICIUM ERINACEUM* AND METHOD OF EXTRACTION**

(75) Inventors: Cun Zhuang, Fort Lee, NJ (US); Hirokazu Kawagishi, Shizuoka (JP); Luyong Zhang, Nanjing (CN); Hideo Anzai, Ridgewood, NJ (US)

(73) Assignee: Masaki Shirota, Paramus, NJ (US)

( * ) Notice: Subject to any disclaimer, the term of this patent is extended or adjusted under 35 U.S.C. 154(b) by 1387 days.

(21) Appl. No.: 12/151,037

(22) Filed: May 2, 2008

(65) Prior Publication Data

US 2009/0274720 A1     Nov. 5, 2009

(51) Int. Cl.
*A61K 35/66*     (2006.01)
*A61K 36/06*     (2006.01)

(52) U.S. Cl.
USPC ........ 435/254.1; 435/171; 424/93.5; 514/783

(58) Field of Classification Search
None
See application file for complete search history.

(56) References Cited

U.S. PATENT DOCUMENTS 5,565,436 A * 10/1996 Kawagishi et al. ............. 514/33
6,287,460 B1 * 9/2001 Van Schie ..................... 210/122

FOREIGN PATENT DOCUMENTS

| JP | 04-266848 | 9/1992 |
|---|---|---|
| JP | 04-275285 | 9/1992 |
| JP | 09-019269 | 1/1997 |
| JP | 09-059171 | 3/1997 |
| JP | 09-059172 | 3/1997 |
| JP | 11-001438 | 1/1999 |
| JP | 11-056300 | 3/1999 |
| JP | 3943399 | 4/2007 |

OTHER PUBLICATIONS

Wang et al., Hypoglycemic effect of extract of *Hericium erinaceus*, 2005, J Science of Food and Agriculture, 85: 641-646.*
Hericenones C, D and E, stimulators of nerve growth factor (NGF)-synthesis, from the mushroom *Hericium erinaceum*, Kawagishi et al. Tetrahedron Letters, vol. 32, No. 35, pp. 4561-4564, 1991.
Chromans, Hericenones F, G and H From the Mushroom *Hericium erinaceum*, Kawagishi, et al., Phytochemistry, vol. 32, No. 1, pp. 175-178, 1993 (printed in Great Britain).
Dilinoleoyl-phosphatidylethanolamine from*Hericium erinaceum* prrotects against ER stress-dependenf Neuro2a cell death via protein kinase C pathway, Nagai, et al. Journal of Nutritional Biochemistry, 17 (2006) 525-530.

* cited by examiner

*Primary Examiner* — Terry McKelvey
*Assistant Examiner* — Catheryne Chen
(74) *Attorney, Agent, or Firm* — Simpson & Simpson, PLLC

(57) ABSTRACT

A fat-soluble fraction extracted from the fruiting body of *Hericium erinaceum* is demonstrated to inhibit the neuronal toxicity of amyloid beta-peptide (Aβ) and induce the synthesis of nerve growth factor (NGF), and has great potential as an active ingredient for pharmaceutical products, health food products, food products and/or beverages to prevent and/or treat dementia, especially Alzheimer-type dementia. This invention is to provide the bioactive fraction and its preparation method.

3 Claims, 3 Drawing Sheets

ANTI-DEMENTIA SUBSTANCE FROM *HERICIUM ERINACEUM* AND METHOD OF EXTRACTION

FIELD OF INVENTION

The present invention relates to the field of bioactive substances derived from natural products. More specifically, the present invention relates to a fraction with anti-dementia effects, especially anti-Alzheimer dementia effects, extracted from the fruiting body of the mushroom *Hericium erinaceum*, and a method for preparing the fraction.

BACKGROUND OF THE INVENTION

Recently, the number of patients with Alzheimer type dementia and cerebrovascular dementia is increasing at a remarkable rate in those countries with a rapidly aging population and this has become a serious social problem. Among these dementias, Alzheimer type dementia occurs due to neurodegeneration. It is symptom-free in its early development period. Once a patient is diagnosed with advanced stages the symptoms are irreversible and incurable with current medical technology. Therefore, a need exists for a bioactive substance that helps to reduce the risk of neurodegeneration and/or to delay the resultant symptoms.

Research is focusing on the clarification of the mechanism under which Alzheimer type dementia progresses and the development of new drugs to treat the condition. There have been a number of reports published. It has been found that patients with Alzheimer type dementia have similar brain abnormalities as those patients with basal forebrain cholinergic neuron syndrome (BFCN) which is also associated with loss of memory and learning capabilities due to neurodegeneration, neuronal atrophy, and neuronal loss. Because nerve growth factor (NGF) exerts a trophic action on BFCN, lack of NGF is considered to be one of the causes of these dementias. However, NGF is a protein, and may be degraded in the body and/or cannot pass through the blood-brain barrier when administrated orally. Therefore, it has become an objective of medical and pharmaceutical researchers in this area to discover or develop substances with low molecular weight which can pass through blood-brain barrier and induce the synthesis of NGF in the brain.

In addition, it has been reported that amyloid beta-peptide (Aβ) is one of the inducers of Alzheimer type dementia since it causes the inflammation and neurodegradation inside the neuron associated with Alzheimer's and leads to death as it accumulates in the brain. Therefore, the inhibition of the toxicities of amyloid beta-peptide is considered to be one of desired ways to prevent and treat the Alzheimer type dementia.

Some investigators have studied the inductive effects of NGF synthesis of *H. erinaceum* extracts. (See, for example, Kawagishi, et al. *Tetrahedron Letters*, 32 (35):4561-4564 (1991); Kawagishi, et al., *Phytochemistry*, 32(1):175-178 (1993); Japanese Patents Nos. 04-266848 and 04-275285.) Other investigators have reported the inhibitory effects of Aβ toxicity of different *H. erinaceum* extracts (See, Nagai, et al. *J. Nutritional Chemistry*, 17:525-530 (2006); Japanese Patent No. 3943399). The cited references all disclose extraction methods that utilize toxic organic solvents in the extraction procedures rendering them problematic for use in industrial or large scale extraction procedures designed to produce compounds for clinical use. In addition, the results disclosed in the references cited above are confined to in vitro experiments.

In this regard, because neurodegenerative diseases typically Alzheimer type dementia have a long incubation period prior to diagnosis, reducing the risk before the identification of visible symptoms of the disease is important. It would be advantageous to be able to reduce the risk of neurodegeneration by the consumption of food products if available and an important of option for target populations. Therefore, there is a need in the field for a method for extracting compounds from *H. erinaceum* using safe chemicals and shown to be effective in vivo.

SUMMARY OF THE INVENTION

The present invention broadly comprises a method for preparing a fat-soluble fraction from *H. erinaceum* by the steps of extracting the fruiting body of *H. erinaceum* with 95% ethanol at room temperature, obtaining the ethanol extract by filtration or centrifugation, concentrating the ethanol extract by removing ethanol under reduced pressure, adding 4~8 volumes of water into the concentrated extract, collecting the resulting floating matter on the surface of the concentrated extract after standing at 4~10 degrees C. for 8~12 hours; and, drying the collected floating matter. The invention also includes a fat-soluble fraction of *H. erinaceum* comprising fat-soluble components that include benzyl alcohol derivatives, chromane derivatives, and phosphatidylethanolamine derivatives with anti-dementia and/or anti-Alzheimer type dementia activities.

In another embodiment, the present invention broadly comprises a bioactive fraction of fat-soluble components of *H. erinaceum* produced by the steps of extracting the fruiting body of *H. erinaceum* with 95% ethanol at room temperature, and obtaining ethanol extract by filtration or centrifugation, concentrating the ethanol extract by removing ethanol under reduced pressure, adding 4~8 volumes of water into the concentrated extract, collecting the resulting floating matter on the surface of the concentrated extract after standing at 4~10° C. for 8~12 hours; and drying the collected floating matter. The bioactive fraction may be incorporated into pharmaceutical products, health food products, food products, and/or beverages. A bioactive fraction is defined as the fat-soluble components of *H. erinaceum* that include anti-dementia and/or anti-Alzheimer's compounds, and found to reduce or eliminate one or more symptoms of dementia and/or Alzheimer's disease.

An object of the invention is to provide a bioactive fraction composed of fat-soluble components that include benzyl alcohol derivatives, chromane derivatives, and phosphatidylethanolamine derivatives as main bioactive compounds.

A second object of the invention is to provide a bioactive fraction having anti-dementia activities, especially anti-Alzheimer type dementia activities, as seen by increased the synthesis of NGF and the reduction or elimination of the toxicity of amyloid beta-peptide.

A further object of the invention is to provide a process of extracting the bioactive fraction that has a high measure of safety.

An additional object of the invention is to provide products that include the bioactive fraction of *H. erinaceum*.

BRIEF DESCRIPTION OF THE SEVERAL VIEWS OF THE DRAWINGS

The nature and mode of operation of the present invention will now be more fully described in the following detailed description of the invention taken with the accompanying drawing figures, in which.

DETAILED DESCRIPTION OF PREFERRED EMBODIMENTS OF THE INVENTION

While the present invention has been described with respect to what is presently considered to be the preferred embodiments, it is understood that the invention is not limited to the disclosed embodiments. The present invention is intended to cover various modifications and equivalent arrangements included within the spirit and scope of the appended claims.

The bioactive fraction of the present invention is obtained by the extraction and fractionation procedures described in Example 1 below in which ground or pulverized fruiting body of the mushroom *H. erinaceum* is extracted with ethanol. The obtained ethanol extract is concentrated by removing ethanol under reduced pressure, and then water is added. The resulting floating matter is collected after standing at 4~10° C. for 8~10 hours. The floating matter is dried to obtain a fraction described in Example 2 below.

Example 1

Figure 1:
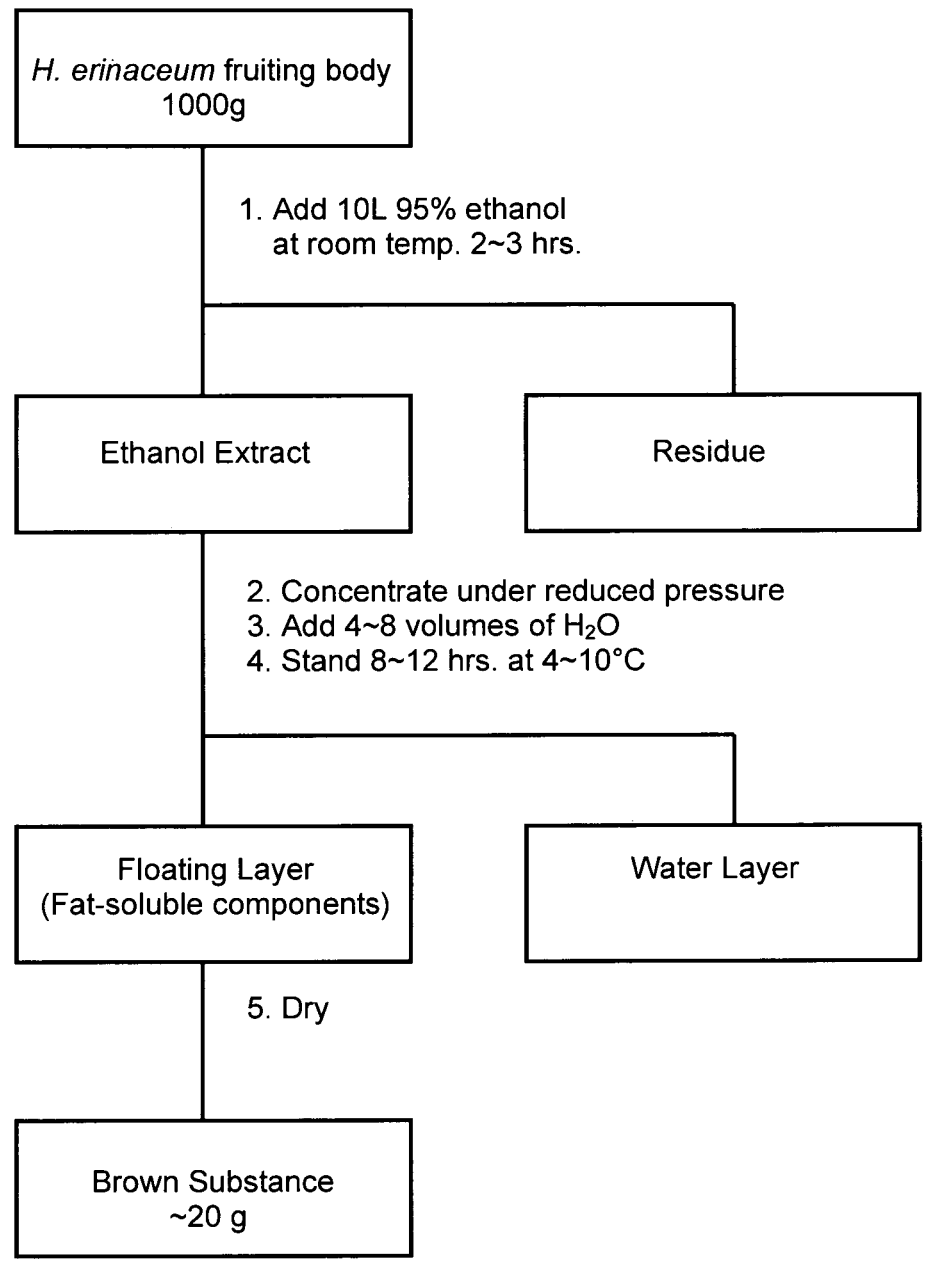
FIG. 1 is a flow diagram depicting the method used to extract the fat soluble fraction from *H. erinaceum*.

The method of obtaining the bioactive fraction of the present invention is described as follows:

As seen in the flow diagram in FIG. 1, 1,000 g of the dried fruiting body of *Hericium erinaceum* was extracted with 10 L of 95% ethanol at room temperature for 2~3 hours, and the ethanol extract was obtained by filtration or by centrifugation. The obtained ethanol extract was concentrated by removing ethanol under reduced pressure, and then 4~8 volumes of water were added into the concentrated ethanol extract. The fat-soluble components separated out from the solution by forming a layer of floating matter on the surface of the solution after standing at 4~10° C. for 8~10 hours. The resulting floating matter was collected by a skimming system or by a pipetting system. The floating matter was dried to yield approximately 19.5 g (dried weight) of brown substance (named as HEF).

Example 2

The fraction of the invention (the floating matter) obtained above in Example 1 was analyzed to identify its characteristics.

The fraction is soluble in methanol or ethanol, insoluble in water, and is thermostable.

The fraction was completely dissolved in 95% ethanol, and chloroform was added into the residual solution after ethanol was removed under reduced pressure. The chloroform-soluble components were obtained by solvent partition between chloroform and water.

Figure 2:
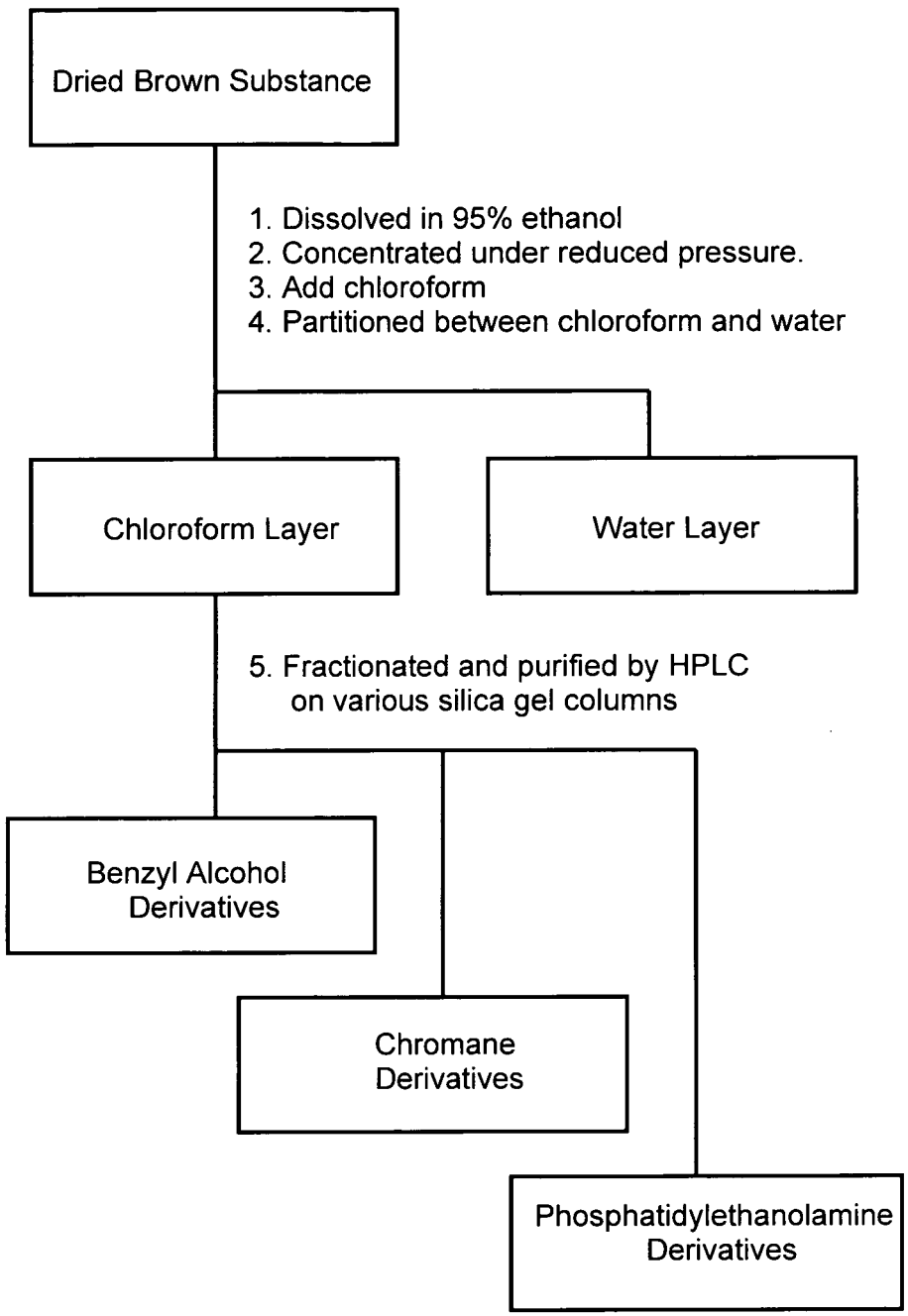
FIG. 2 is a flow diagram depicting the method used to fractionate the fat soluble fraction obtained from *H. erinaceum*; and, FIG. 3 is a graph showing the effects on cell viability after administration of increasing doses of HEF.

As seen in FIG. 2, the chloroform-soluble components were fractionated and purified by high performance liquid chromatography (HPLC) on various silica gel columns. The purified compounds were determined using Fast Atom Bombardment Mass Spectrometry (FAB-MS), IR spectrum (IR) and Nuclear Magnetic Resonance (NMR) methods well known to those having skill in the art, and identified as benzyl alcohol derivatives, chromane derivatives, and phosphatidylethanolamine derivatives, respectively.

The following examples describe several experiments performed in order to investigate the biological activities of the substance of this invention (HEF).

Example 3

Six groups of Sprague-Dawley male rats approximately 11 weeks old were divided into control, amyloid beta-peptide (Aβ), Aβ+Donepezil (Aβ+D), Aβ+HEF-H (high dose), Aβ+HEF-M (middle dose), and Aβ+HEF-L (low dose) groups. The rats of the Aβ, Aβ+D, Aβ+HEF-H, Aβ+HEF-M, and Aβ+HEF-L groups were separately injected with 5 μL of amyloid beta-peptide ($A\beta_{1-40}$) solution at a concentration of 2 μg/μL into both sides of brain hippocampus for preparing the rats with Alzheimer type dementia (AD rats). The control group was injected with 5 μL of saline. From the fourth day after the injection, the Aβ+D group was administered with the anti-Alzheimer's drug Donepezil (brand name: Aricept) at a dose of 1 mg/kg (equal to 2 times of the recommended therapeutic dose clinically), and Aβ+HEF-H, Aβ+HEF-M, and Aβ+HEF-L groups with HEF separately at the doses of 24 mg/kg, 12 mg/kg, and 6 mg/kg, and the control and Aβ groups with same volume of saline by stomach tube once per day for four weeks. From the fourth week after the administration, learning and memory-related behavior was assessed using the Morris Water Maze Test on ten rats arbitrarily-chosen from each group once a day for one week (from day 1 to day 6 the time to arrive at the platform is measured, and on day 7 the platform is removed and the frequency to cross (pass by) the platform location is counted). After completing the behavioral test, the rats were sacrificed. The cerebral tissues separated from half of the rats of each group were used for pathological examination, and the olfactory bulb, hippocampus, locus ceruleus, and cerebral cortex from another half were used to determine the NGF content with enzyme-linked immunosorbent assay (ELISA).

The results of Morris Water Maze Test are shown in Table 1 and Table 2 below.

TABLE 1

Results of Morris Water Maze Test on $A\beta_{1-40}$-induced AD rats from day 1 to day 6 (n = 10)

| Groups | Arrival Time of Platform (Second) | | | | | |
| --- | --- | --- | --- | --- | --- | --- |
| | Day 1 | Day 2 | Day 3 | Day 4 | Day 5 | Day 6 |
| Control | 68.75 ± 21.69 | 29.23 ± 14.28 | 16.96 ± 11.41 | 14.63 ± 7.17 | 17.58 ± 10.87 | 15.03 ± 7.69 |
| Aβ | 83.80 ± 19.65** | 55.03 ± 22.13** | 43.23 ± 31.39** | 53.53 ± 22.13** | 48.68 ± 22.95** | 49.73 ± 26.07** |
| Aβ + Donepezil | 77.03 ± 29.92 | 39.10 ± 26.36## | 34.98 ± 23.42 | 31.10 ± 23.26## | 30.00 ± 21.11## | 28.43 ± 23.45## |
| Aβ + HEF-H | 74.98 ± 27.89 | 40.45 ± 20.93## | 34.58 ± 24.64 | 29.73 ± 22.78## | 29.68 ± 19.55## | 26.96 ± 22.35## |

TABLE 1-continued

Results of Morris Water Maze Test on $A\beta_{1-40}$-induced AD rats from day 1 to day 6 (n = 10)

| Groups | Arrival Time of Platform (Second) | | | | | |
|---|---|---|---|---|---|---|
| | Day 1 | Day 2 | Day 3 | Day 4 | Day 5 | Day 6 |
| Aβ + HEF-M | 79.65 ± 20.05 | 45.98 ± 21.65 | 38.45 ± 20.46 | 38.80 ± 19.78## | 34.58 ± 21.83## | 35.23 ± 24.67# |
| Aβ + HEF-L | 86.53 ± 27.08 | 50.95 ± 21.85 | 44.45 ± 31.45 | 48.13 ± 24.10 | 40.83 ± 19.91 | 39.23 ± 26.89 |

*$P < 0.05$,
**$P < 0.01$, Compared to control group;
$P < 0.05$,
$P < 0.01$,
Compared to Aβ group

TABLE 2

Frequencies of crossing platform location within two minutes on day 7 (n = 10)

| No. | Group | | | | | |
|---|---|---|---|---|---|---|
| | Control | Aβ | Aβ + Donepezil | Aβ + HEF-H | Aβ + HEF-M | Aβ + HEF-L |
| 1 | 7 | 3 | 8 | 6 | 8 | 8 |
| 2 | 4 | 2 | 6 | 6 | 11 | 6 |
| 3 | 6 | 5 | 10 | 11 | 14 | 6 |
| 4 | 7 | 3 | 7 | 7 | 4 | 6 |
| 5 | 8 | 10 | 14 | 13 | 6 | 10 |
| 6 | 12 | 12 | 11 | 12 | 11 | 2 |
| 7 | 21 | 4 | 22 | 26 | 15 | 4 |
| 8 | 15 | 4 | 19 | 7 | 12 | 16 |
| 9 | 21 | 2 | 10 | 15 | 13 | 8 |
| 10 | 18 | 7 | 13 | 11 | 4 | 4 |
| Mean ± SD | 11.90 ± 6.44 | 5.20 ± 3.43** | 12.00 ± 5.16## | 11.40 ± 6.02# | 9.80 ± 4.05# | 7.00 ± 3.92 |

*$P < 0.05$,
**$P < 0.01$,
Compared to control;
$P < 0.05$,
$P < 0.01$,
Compared to Aβ

The Aβ group took a significantly longer time to arrive at the platform from day 1 to day 6 (Table 1), and showed lower frequencies in crossing the platform location within 2 minutes on day 7 (Table 2) as compared with the control (p<0.01), which was correlated with the memory impairment in the rats of Aβ group due to the injection of $A\beta_{1-40}$. Comparing the treatment groups with Aβ group, the escape latencies of Aβ+D, Aβ+HEF-H, and Aβ+HEF-M groups were improved from day 1 to day 6, in particular, remarkably decreasing the time needed to arrive to the platform from day 4 to day 6 (p<0.01) and increasing the frequency of crossing the platform location on day 7 (P<0.01 or P<0.05). Also, Aβ+HEF-L showed fewer escape latencies from day 4 to day 6 and higher frequencies on day 7 compared to Aβ group.

These results demonstrated that the fat-soluble fraction of *H. erinaceum* has the ability to improve recognition of space and memory in AD rats.

As shown in Table 3, after four weeks of treatment, the NGF content of the olfactory bulb, hippocampus, locus ceruleus, and cerebral cortex of the rats in all of treatment groups including Aβ+D, Aβ+HEF-H, Aβ+HEF-M, and Aβ+HEF-L had higher average values of NGF as compared to those in control and Aβ groups. In particular, the NGF content of the hippocampus and cerebral cortex in Aβ+D, Aβ+HEF-H, and Aβ+HEF-M groups showed significant increases (P<0.01 or P<0.05).

TABLE 3

NGF contents of cranial nerve nucleus of $A\beta_{1-40}$-induced AD rats (n = 10)

| Group | NGF content (ng/g cranial nerve nucleus) | | | |
|---|---|---|---|---|
| | Olfactory bulb | Hippocampus | Locus ceruleus | Cerebral cortex |
| Control | 9.20 ± 3.09 | 9.82 ± 3.56 | 2.43 ± 0.64 | 5.08 ± 1.59 |
| Aβ | 9.89 ± 1.80 | 10.65 ± 2.33 | 2.46 ± 0.45 | 5.80 ± 0.98 |
| Aβ+Donepezil | 10.11 ± 2.10 | 14.20 ± 4.14* | 3.07 ± 1.38 | 6.79 ± 1.10* |
| Aβ+HEF-H | 10.89 ± 1.75 | 16.23 ± 6.16* | 3.14 ± 0.95 | 7.59 ± 1.60** |

TABLE 3-continued

NGF contents of cranial nerve nucleus of $A\beta_{1-40}$-induced AD rats (n = 10)

| Group | NGF content (ng/g cranial nerve nucleus) | | | |
|---|---|---|---|---|
| | Olfactory bulb | Hippocampus | Locus ceruleus | Cerebral cortex |
| Aβ+HEF-M | 10.72 ± 2.39 | 15.14 ± 5.92* | 2.71 ± 0.76 | 6.69 ± 0.56* |
| Aβ+HEF-L | 10.10 ± 1.91 | 11.54 ± 4.31 | 2.58 ± 0.85 | 5.90 ± 1.91 | mean ± SD;
n: Number of rats;
*P < 0.05,
**P < 0.01, Compared to Aβ

Example 4

Recently, it has been reported that the neuronal cytotoxicity of amyloid beta-peptide is very involved with oxidation stress and endoplasmic reticulum (ER) stress. Tunicamycin is a protein glycosylation inhibitor and generally used as an inducer of ER stress. This experiment was conducted to investigate if HEF protects against ER-dependent neuro2a cell death.

Neuro2a cells were cultured in a 96-well plate with Dulbecco's modified eagles medium at a cell density of 5,000 cells/well. After 1 day of culture at 37° C., 0.5 µg/mL of tunicamycin (Wako, Japan) at varying concentrations (1 µg/mL or 10 µg/mL) of HEF was added to the medium. The cells were incubated for 24 hours, and then the viability was measured by 3-(4,5-dimethyl-2thiazolyl)2,5-diphenyl-2H-tetrazolium bromide (MTT) assay.

Figure 3:
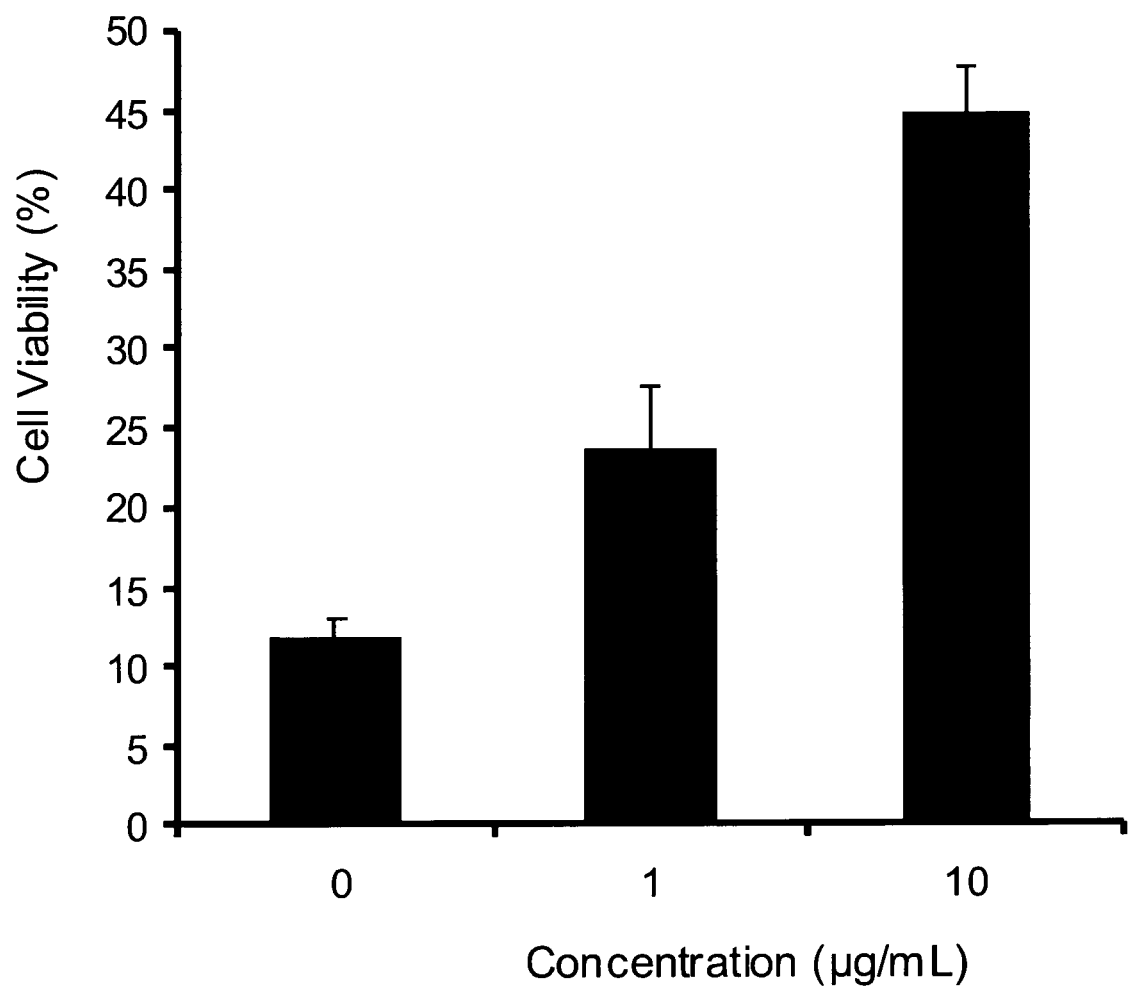

As shown in FIG. 3, the cell viability decreased to 11.6% after treated with tunicamycin, whereas the addition of 1 µg/mL and 10 µg/mL of HEF increased the viability to 23.34% and 44.8% respectively. The result suggests that HEF may protect neuron from the cytotoxicity of amyloid beta-peptide by reducing ER stress

Example 5

Five-week old male and female mice of the ICR strain were used in the experiment. Five each of male and female mice were allocated to each group, and the mice were not fed for about four hours prior to treatment and then each was weighed. To the mice of the test group, HEF suspended in saline was administered orally with a stomach tube at a dose of 300 mg/kg. To the control group, the same volume of saline was administered in the same manner as in the test group. Clinical observations were made during 14 days of the experiment period, and at the end of the experimental period all mice were sacrificed for internal organ examination.

Throughout the experimental period, no animal death, no abnormalities in general their general condition, and no significant difference in the mean body weight were observed in either males or females after the treatment. Also, no noteworthy changes were found in any organ of either males or females in any of the internal examinations. Consequently, it was concluded that the LD50 of the HEF was higher than 300 mg/kg at a single dose.

Example 6

Nine-week old male and female rats of the Sprague-Dawley strain were used in the experiment. Ten each of male and female rats were allocated to the control, HEF-H (high dose), HEF-M (middle dose), and HEF-L (low dose) groups. To the rats of HEF-H, HEF-M, and HEF-L groups, HEF suspended in 0.5% sodium carboxymethylcellulose (CMC-Na) was administered orally with a stomach tube separately at the doses of 120 mg/kg, 60 mg/kg, and 7.2 mg/kg once per day and 6 times a week for 13 weeks. To the control group, the same volume of 0.5% CMC-Na was administered in the same manner. Body weight was measured once a week and the dose was adjusted based on the increase of body weight. Clinical observations were made during the 13 weeks of the experimental period, and at 24 hours after the end of the experiment period, each group was divided into two subgroups (five each of male and female). Blood was drawn from one subgroup for hematological and biochemical analyses, and then these rats were sacrificed for internal organ examination. The members of the second subgroup were kept breeding without HEF for 4 weeks of recovery period. At the end of the recovery period, blood was drawn for the hematological and biochemical analyses and all rats were then sacrificed for internal organ examination.

Throughout the experimental and recovery periods, no animal death, no abnormalities in general condition, and no significant differences in the mean body weight were observed in either males or females. Also, no noteworthy changes were found in the hematological and biochemical analyses and in any organ of either males or females in any of the internal examination.

Effect of the Invention

In the method of this invention, the process to obtain fat-soluble components by adding water into the concentrated ethanol extract is an important improvement over the use of toxic organic solvent fractionation used in the prior art. The method of this invention is safer and easier for use in industry compared to those described in the prior art and appears to possess a more stable yield rate.

The fat-soluble fraction obtained by the method disclosed above is demonstrated to act not only as an inducer of NGF synthesis but also as an inhibitor of amyloid beta-peptide toxicity. Such both bioactivities have never been found simultaneously in any active compounds as described in prior patents and publications.

The fat-soluble fraction of this invention has significant anti-dementia effects on AD rats when administered orally. Therefore, the fraction may be useful for prevention and improvement of dementia, especially Alzheimer type dementia, and for improvement of memory loss and lack of acuity.

The fraction of this invention shows no toxicities in single-dose toxicity test and 90 days repeated dose toxicity test indicating it is safe for use in in vivo administration.

The fraction of this invention is able to be used as an active ingredient for pharmaceutical and/or health food products in tablet, capsule, granule, tincture, and beverage forms. For tablet, hard capsule, and granule manufacturing, the fraction may be combined with excipients such as, but not limited to, dicalcium phosphate, sucrose fatty acid ester, microcrystalline cellulose, lactose, silica or other inactive fillers and binders well known to those skilled in the art. For soft capsules, the fraction may be combined with excipients, such as, but not limited to, vegetable oil, while in liquid form, carriers including, but not limited to, glycerin and ethanol may be used as solvent of the fraction. Methods of manufacturing all the above product configurations are known to those skilled in the art.

In addition, it should be noted that a variety of health food products can be formulated by combining the fraction of this invention with other active ingredients such as, but not limited to Ginkgo, Docosahexaenoic acid (DHA), Phosphatidylserine, Choline as well as other medicinal mushrooms, herbs, vitamins, unsaturated fatty acids, phospholipids, choline, and minerals.

Further, the fraction of this invention that includes derivatives of benzyl alcohol, chromanes, and phosphatidylethanolamine can be used as an additive for health foods, general food products, and beverages. This fraction can be used not only for health foods or beverages designed for humans but also for animal feed.

Thus it is seen that the objects of the invention are efficiently obtained, although changes and modifications to the invention should be readily apparent to those having ordinary skill in the art, which changes would not depart from the spirit and scope of the invention as claimed.

We claim:

1. A method for preparing a fat-soluble fraction of the fruiting body of *Hericium erinaceum* comprising in order the steps of:
    extracting the fruiting body of *H. erinaceum* with 95% ethanol at room temperature;
    separating said ethanol extract by filtration or centrifugation;
    concentrating said ethanol extract by removing ethanol under reduced pressure;
    adding 4~8 volumes of water to said concentrated ethanol extract;
    allowing said mixture of 4~8 volumes of water and said concentrated ethanol extract to stand at 4~10° C. for 8~10 hours;
    collecting the resulting floating matter on the surface of said concentrated extract; and, drying said collected floating matter.

2. The method for preparing a bioactive fraction as recited in claim 1 wherein said collection of the resulting floating matter is performed by skimming.

3. The method of preparing a bioactive fraction as recited in claim 1 wherein said fat-soluble fraction includes benzyl alcohol derivatives, chromane derivatives, and phosphatidylethanolamine derivatives.

* * * * *